United States Patent
Benado

(10) Patent No.: US 6,395,114 B1
(45) Date of Patent: May 28, 2002

(54) METHOD OF MAKING NATURAL BOTANICAL SCULPTURE

(76) Inventor: Anna Marie Benado, 631 W. Fm 389, Fayetteville, TX (US) 78940-5045

( * ) Notice: Subject to any disclaimer, the term of this patent is extended or adjusted under 35 U.S.C. 154(b) by 0 days.

(21) Appl. No.: 09/411,153

(22) Filed: Nov. 29, 1999

(51) Int. Cl.$^7$ .................................................. A01N 3/00
(52) U.S. Cl. ............................ 156/61; 427/4; 428/22; 428/24; 504/114
(58) Field of Search ............................. 156/61; 427/4; 428/22, 24; 504/114; A01N 3/00, 3/02, 3/04

(56) References Cited

U.S. PATENT DOCUMENTS

| | | | | |
|---|---|---|---|---|
| 996,788 A | * | 7/1911 | Ostrander | 427/4 |
| 1,779,299 A | * | 10/1930 | Valentine | 427/4 |
| 4,783,342 A | * | 11/1988 | Polovina | 427/4 |
| 6,265,346 B1 | * | 7/2001 | Reeves et al. | 504/114 |

FOREIGN PATENT DOCUMENTS

JP    59-44301 A   *   9/1982

OTHER PUBLICATIONS

Shields, J. ,Adhesives Handbook, CRC Press 1970, p. 36.*

* cited by examiner

*Primary Examiner*—Jeff H. Aftergut
(74) *Attorney, Agent, or Firm*—Lisa N. Benado

(57) ABSTRACT

A method for making a natural botanical sculpture that captures the plant's form and beauty is provided. A plant or plant part is used as an armature in the creation of a durable representation of the plant. The outer surface of the organic material is plastered with a viscous paste composition that includes composed of an adhesive, a synthetic latex resin prepared by emulsion polymerization, and a thickener. The paste dries to produce an inflexible and air-tight encasement. The plant is permanently preserved within the encasement.

17 Claims, No Drawings

METHOD OF MAKING NATURAL BOTANICAL SCULPTURE

FIELD OF THE INVENTION

The present invention relates generally to a natural botanical sculpture, and more particularly to a method for encasing cut plants and plant parts to form a durable plant form.

BACKGROUND

The aesthetic value of botanicals has long been appreciated. Botanicals, such as plants and parts or plants, e.g. flowers, stems, seeds, leaves, vegetables, fruits, etc. are commonly used for gifts, decorative purposes, museum specimens, educational purposes and the like. Some plants are present during special occasions and thus also have sentimental importance.

However, the enjoyment of many plants is hampered by their short lives. When botanicals die, they lose their pleasing appearance. Cut flowers that have their stems submersed in water usually survive only for a few days to a several weeks, barring any further treatment. As a result, much effort has been made to preserve and prolong the life of plants.

In order to sustain a plant's appearance, a drying process is often employed to remove most of the plant's water supply. The drying process may be carried out by immersing the plant into a drying agent, such as a dehydrating alcohol or a dessicating substance, e.g. silicone fluid or gel, silicone resin, alkaline formaldehyde sulfoxyate, aluminum or magnesium sulphate and cupric or other transitional metal sulphate and isoniazid. In addition, the plant may be freeze dried or exposed to low-humidity air. Dehydration may take place by exposure to vacuum pressure such as 100 mm Hg. A combination or these processes may also take place. See U.S. Pat. Nos. 5,421,121; 5,399,392; and 5,366,954.

However, drying processes cause the plants to become extremely brittle, fragile and highly susceptible to damage in extremes of temperature or humidity. Special handling and storage techniques of the dried plants are required. Some dried plants undergo further treatment in attempts to increase the durability of the plants. For example, the plant may be reacted with a cross-linking compound to form a polymeric network. See European Pat. Appl. No. 87309407.2.

The dried plants also relinquish their shape by drastically shrinking in size and curling of tissues such as leaves and petals. Furthermore, the natural colors of the plants are inclined to fade during dehydration. The natural beauty of the plants is forfeited and their value as decorative items is reduced.

Many other current approaches endeavor to maintain the natural appearance of the plant to keep them looking "alive" and simply extend the shelf-life and display-life of plants. Some of these advances involve adding a preservative agent to the water solution into which the cut stem, stalk, trunk or vine of a physiologically active plant is immersed. In other processes, the entire plant is totally immersed in the solution. The plant uptakes the solution by pulling the fluid from a container into the tissues of the plant. The preservative acts as a humectant by replacing the fluids and electrolytes which were supplied to the xylem by the root system. One exemplary humectant is an ethylene glycol solution. See U.S. Pat. Nos. 5,723,407; and 5,798,150.

However, glycerol infusion frequently results in bleeding or weeping of the solution from the plant surfaces, especially in environments of high humidity. Such humectants also may cause color changes in the plant. Some attempts to resolve the color loss problem include the infusion of dyes in solution with the humectant. See U.S. Pat. No. 5,807604.

A thin clear coat barrier of film may be added to the plant surface to prevent leakage of dye and humectant. In still other approaches, an acrylic polymer film that permits moisture transmission is coated over the plant. The film has sufficient oxygen and carbon dioxide permeability to support respiration of the plant. See U.S. Pat. No. 4,783,342.

Although these methods extend the life of the plant, the resulting plant is not a durable and permanent article. Even with a thin film covering, the plants remains susceptible to breakage and fluctuations in environmental temperature and humidity.

Thus, there is still a need for a method of creating a permanent and tough plant form that will endure drastic environmental condition and withstand substantial pressure. It would be beneficial for such a plant form to maintain the general structure and color of the original live plant.

SUMMARY OF THE INVENTION

A natural plant sculpture having a plant armature fixed within a hardened paste encasement is provided. In one embodiment, the sculpture resembles the structure of the underlying plant, but takes on a porcelain-like image. Rather than the preserved plant appearing alive, this durable object is created in the plant's likeness by using the encased plant as a mold. The sculpture is developed, according to the present invention, by plastering a surface of the plant or plant part with one or multiple paste layers. Each paste layer is dried to a hard finish. A sufficient number of paste layers are spread on the surface to render the sculpture product inflexible and durable. The final encasement is airimpermeable. Each paste layer is usually at least substantially dry before application of the subsequent layers. Often the final encasement is between about 0.50 mm and 5.00 mm in thickness, but thinner or thicker encasements are possible as long as the shell is rigid.

The paste is comprised of an adhesive, a synthetic latex resin prepared by emulsion polymerization, and a thickener. In one composition of paste, the latex is selected from the group comprising homopolymers and copolymers of vinyl esters, acrylate and methacrylate esters, maleic acid, maleic anhydride and maleic acid esters. In another paste composition, the latex is a vinyl acetate resin emulsion. In still other embodiments of paste, the thickener component is starch and/or the adhesive ingredient is glue.

The paste is usually applied in a manner that minimizes damage to the plant. Thus, a brush, sponge, cloth, cotton or other similar utensil may be used to spread on paste to the plant surface. Often, a portion of the plant is contacted with an aqueous solution as another portion of the plant is treated with paste. In one exemplary case, the cut end of a flower stem immersed in water as the remaining petals, leaves, stem, etc. are covered with paste.

In still other embodiments of the method, paint is spread over the dried encasement. The plant sculpture may also be made waterproof by coating a water-insoluble sealer over the painted or unpainted dried encasement.

The benefits of the natural plant sculpture are direct in that the plant form is presumably permanent, tough, enduring of drastic environmental condition and withstanding of substantial pressure forces. In some embodiments, the sculpture maintains the general structure and color of the original live plant. In other embodiments, a new artificial color or design may be added to the sculpture.

Other features and advantages of these and other embodiments are discussed in detail below.

DETAILED DESCRIPTION

A method for making a natural botanical sculpture that captures the plant's form and beauty is provided. A plant or plant part is used as an armature in the creation of a durable representation of the plant. The outer surface of the organic material is plastered with a viscous paste composition that solidifies to produce an inflexible and air-tight encasement having the general form of the original plant. In some embodiments, the product maintains the natural color of the enclosed plant. The paste of the present invention is applied by spreading one layer or multiple layers of the paste over the plant surface in a manner that minimizes damage to the plant.

The present method of making a botanical sculpture may be practiced with any botanical including plants or portions of plants, such as flowers, stems, seeds, leaves, vegetables and fruits that may benefit from a preserved appearance. For simplicity of describing the present invention, the term "plant" is herein intended to include all organisms or part of organisms in the kingdom plantae, e.g. flowering plants, conifers, ferns, mosses, etc., but also includes related botanical kingdoms, such as the kingdom fungi, e.g. lichens, mushrooms, mold, etc. and the kingdom protista, e.g. algae, sea weed, etc.

Firm plants impart convenience of use with the techniques provided because damage to the plant tissue during the formation of the sculpture is easily avoided. However, the present methods are well suited for applications with delicate plant armatures, such as flower petals, as well. The use of fresh plants permits the sculpture to closely resemble the natural color and structure of the plant. For example, newly opened flowers may be chosen to capture the flower's general form.

The plant has an accessible surface area that may be composed of any organic matter and have any texture, i.e. smooth, rough, glossy, fuzzy, etc. In general, the outer plant tissue is made up of a protective epidermis of a layer of cells. The surface of some woody stems, such as dogwood, is an outer protective layer of tough bark that is perforated with lenticels to allow gas exchange. The surface of leaves typically include a cuticle covering the epidermis. Some fruits have outer exocarp layers. Other fruits have a dry pericarp to surround their seeds. The present invention is well suited for these or other plant surfaces.

In one embodiment of a natural plant sculpture, the plant is a flower, for example, a rose, daisy, carnation, sunflower or other flower. The petals, reproductive structures, e.g. anther and stigma, and stem have surfaces upon which an initial layer of the latex emulsion-based paste is provided. This initial layer may serve to seal the pores present on the flower surface. In some embodiments, a single layer of paste is a sufficient to provide an inflexible and air tight encasement and the plant only includes this sole layer of paste.

In other embodiments, multiple layers of paste are provided. For example, two to five or more layers may be needed to provide additional support, seal, structure and rigidity to the sculpture. Thus, use of multiple layers rather than one thick layer may be beneficial where the plant is delicate. Thus, where the plant armature has delicate tissues, multiple thin layers may be chosen to avoid weighing down the plant tissue and causing damage to the plant.

The hardened layers of paste form an encasement having the general form of the underlying flower. The plant sculpture is not frangible but rather is rigid and inflexible. By the term "inflexible" it is meant that the encasement in not pliable and resists breaking or cracking with application of substantial pressure compared to the pressure that damages uncoated plants.

An exceptional quality to the sculpture of the present invention is that the hardened encasement retains its form, even where uncovered portions of the plant wilt and crumble. Thus, once the paste dries, the original plant form is not needed to maintain the sculpture. For example, outer flower petals and the stem may be covered with paste and not the internal petals and reproductive structures. In this case, the uncovered structures die off and the covered portions remain as the sculpture product. Care should be taken to plaster enough of the plant to allow the resulting sculpture to be freestanding.

Often the sculpture has a porcelain-like finish. The encasement may be clear and permit the sculpture to exhibit the natural color of the plant armature. However, some plants undergo color changes to different hues or fade during the process.

The sculpture product is permanent and durable. Exemplary sculptures have been found to last over five years in extreme fluctuations of humidity and temperature e.g. less than 20° F. to greater than 100° F., without any signs of deterioration. Furthermore, sculptures including delicate flower armatures may withstand at least substantial amounts of weight without collapsing or cracking as compared to the amount of weight required to damage untreated plants. For example, the sculpture may endure at least 3 to 5 times the weight that would typically cause damage to the same plant that is not layered with an encasement.

The thickness of the encasement may vary as desired to produce an inflexible seal. The thickness is typically not so great as to totally lose the general form of the original plant shape. Generally, the encasement thickness is between about 0.50 to 10.00 mm, usually about 0.50 to 5.00 mm, and more usually about 1.00 to 2.00 mm, as provided by a covering of either one or multiple paste layers over the plant surface. The encasement may be of varying thickness in different parts of the plant. An exemplary single layer may be about 1.00 to 2.00 mm when wet and 0.30 to 1.00 mm when dry. However, thinner or thicker encasements and paste layers are possible as long as the resulting sculpture is not pliable and seals out air.

Paste Composition

The paste is composed of an adhesive, a synthetic latex resin prepared by emulsion polymerization and a thickener. The paste is water-soluble and dries to a hard and durable finish. Often the paste is relatively clear when dry and non-toxic.

The adhesive may be epoxy, glue, cement or other similar substance. Typically, the adhesive is glue, such as white glue (Dap Weldwood Hobby n' Craft Glue, Dap Inc. located in Dayton, Ohio, subsidiary of USG Corp.). It has been observed that the use of glue without the latex emulsion and thickener creates layers that are too thin and drips off the plant surface.

The latex emulsion is prepared by known methods of emulsion polymerization. Various well known latex emulsions may be utilized. Homo and copolymers of vinyl esters, acrylate and methacrylate esters, maleic acid, maleic anhydride, and maleic acid esters are found particularly effective. Such materials, for example, may include vinyl acetate homopolymers and copolymers of the same with ethyl and butyl acrylates and methacrylates as well as dibutyl maleate. One exemplary material comprises about 92.5 percent by weight of an approximately 55 percent nonvolatile polyvinyl acetate aqueous latex including conventional stabilizers with about 7.5 percent dibutyl phthlate or other conventional plasticizers. Often the latex emulsion is plasticized polyvinyl acetate latex emulsion prepared by emulsion polymerization. Techniques for forming latex emulsions are well known by those skilled in the art. An exemplary latex emulsion is Mod Podge®, Matte or Glossy, and preferably Matte, by Plaid Enterprises, located in Norcross, Ga.

The latex emulsion adds durability to the final product. However, it has been noted that the use of the latex emulsion without the adhesive and thickener is inadequate to create the intended plant sculpture because the latex has difficulty adhering to organic surfaces, especially surfaces with smooth textures. The latex tends to slide off of the plant surface. Furthermore, the latex may result in balls rather than a smooth coating. A plant covered with the latex alone also does not hold its shape. Moreover, the latex often reacts with flowers causing them to wilt, possibly by absorbing through the porous tissue surface. By contrast, the paste composition, according to the present invention, does not infuse into the internal plant tissue but rather remains adhered to the external plant surface.

The thickener may be any substance known to those skilled in the art that creates a viscous consistency, such as gum or starch. The thickener is usually a starch, such as Argo® Corn Starch, from Best Foods, Division, CPC International Inc., located in Englewood Cliffs, N.J. The use of starch allows the paste to turn translucent when dry. Typically, the thickener is mixed with water to form the desired consistency. The consistency of the thickener prevents the paste from being so dilute that the composition falls off the plant surface or weigh down delicate tissues. The use of starch alone, and without the adhesive and latex emulsion, is unsatisfactory to create a plant sculpture because the product is not durable and dries to a cracked and white opaque finish.

It is further observed that the combination of the thickener and adhesive, absent the latex emulsion, fails to create an air-tight seal. As a result, the underlying plant loses its color and usually turns brown. In order to create an air-free encasement without use of latex, the shell covering is too thick to adequately represent the plant form and is typically opaque in color.

The paste composition is prepared by mixing the ingredients in various proportions to form the desired viscous consistency. The intended consistency depends, inter alia, on the type of plant armature, the plant's surface composition and texture, the desired appearance of the product, etc. Typically, the composition has a batter-like viscosity which must be manually spread over the plant surface. The paste also has an elastic quality that allows the composition to be drawn out over the intended surface.

The component amounts and proportions may be easily determined by one skilled in the art. The amount of adhesive is not so great as to make the paste too sticky to conveniently handle. Excessive adhesive may also cause undesirable sagging of delicate tissues and may not harden to a durable finish. Similarly, the amount of latex emulsion should not be excessive so as to cause delicate tissues to remain limp and lose their shape. Too much latex emulsion may further result in less viscous paste that drips and runs off of plant surfaces. The amount of thickener is also not so great as to create a brittle encasement that tends to crack. The thickener amount should also permit the paste to transition from white to clear in color.

In one exemplary method of preparing the paste, the thickener is warmed and added to the latex emulsion. The combination is thoroughly mixed to a smooth consistency. While the latex mixture is still warm, the adhesive is then blended with the latex mixture until the paste composition cools to room temperature. However, the present invention anticipates any order of ingredients to be combined and at any suitable temperature.

Method of Making the Sculpture

The operative steps in constructing the plant sculpture include spreading the paste over the plant surface and drying the paste to a hardened shell. The optimal environment for the process is low humidity, but the process may be successfully carried out in extreme variations of humidity and temperature.

The entire plant may be treated at one time, or various portions of the plant may be coated at varying time intervals. For example, flower petals may be coated and allowed to dry, and then the flower stem and leaves may be treated. In another embodiment particularly useful with delicate plants, one side of a plant part, such as a petal, is plastered and dried and then the opposite surface is covered.

A sufficient amount of paste is applied to the plant in layers to create an inflexible and air-tight encasement. The term "sufficient amount" as used herein, means the minimum amount necessary to cause a particular event, e.g. to form an inflexible and air-tight encasement.

In order to maintain the freshness of the plant, a portion of the plant may be in contact with an aqueous solution during the layering process. The paste may be spread over the plant surface using a variety of techniques that minimize damage to the plant. The term "spread" is meant to include painting, smearing, dabbing, stroking, extruding, or other similar techniques in which a layer of the paste is extended over the plant surface. Usually, the paste is painted onto the plant surface with a utensil, such as a brush, sponge, cloth, mitt, cotton, and the like. Spreading of paste by hand is preferred, but the process may also be performed by automated instrumentation. Although, the plant may be dipped into the paste composition, usually due to the viscous nature of the paste, the plant tissue becomes damaged and the amount of the paste applied is not easily controlled. Similarly, usually the viscosity of the paste does not permit spraying of the composition.

Usually, each layer of the paste is cured by various methods so that the composition is at least substantially dry to the touch before applying subsequent layers. The layer is usually completely dry, but also may be slightly sticky. In some embodiments, the individual paste layers are given 10 to 30 minutes to dry between subsequent addition of layers. The final top layer of paste is allowed to completely dry to form a firm covering. Typically the paste is allowed to air dry at room temperature. But a higher temperature, a dry environmental climate, circulating air and/or exposure to an air conditioner may be used to facilitate the drying process. Often, the paste is white when wet and dries to a clear finish. The use of a quick drying step promotes the stabilization of the plant's natural color.

The inclusion of various enhancement steps is within the intended scope of the invention to create other embodiments of the sculpture. In one such variation artificial color is added to the creation. Usually, color is added after the encasement dries with conventional paint, e.g. an oil-based or acrylic paint, such as by Sherwin-Williams, Corp., Crylon Products Group located in Solon, Ohio. The paint may be brushed, sprayed or otherwise extruded or spread over the encasement. The chosen color may imitate the original color of the plant or be a contrasting color to create a particular desired effect. For example, a Metallic Paint or Classic Pearls by Plastic-Kate Corp. located in Media, Ohio. Although, dye additives included in the paste composition may be used to enhance color of the sculpture, the resulting coloration is usually uneven with multiple paste layers.

Other various effects may be achieved by techniques to create textured or other finishes. For example, the paste may be applied using heavy brush strokes or stippling. Furthermore, prior to the outer layer becoming fully dried, the layer may be contacted with a textured surface or designs may be carved out of the layer with a utensil. In other embodiments, an applicator e.g. pen or fine brush, is used to inscribe or draw with ink or paint onto the dried sculpture.

Furthermore, the sculpture product may be finally coated with a water-insoluble sealer, such as an acrylic or enamel sealer, to protect the waterproof the encasement. A thin layer of the sealer may be sprayed over the dried plant encasement.

EXAMPLES

1. Preparation of Paste Composition

About 1.25 cup of spring water provided at room temperature is mixed with 1.00 cup of cornstarch in a double boiler container such that the liquid in the lower container gently boils and the mixture in the top container is over low heat. The heat is gradually increased while beating slowly with a conventional electric beater and scraping the mixture from the sides and bottom of the container to ensure that the starch is smooth. When the mixture becomes very thick and glossy, the mixture is removed from the heat. About 0.75 cup of Mod Podge Matte is very slowly added to the mixture. The mixture is beat well to maintain a smooth consistency. Finally, about 1.00 cup of Dap Weldwood white glue is slowly added to the mixture and the composition is mixed. The container is covered and the composition is cooled. The mixture is continued to be beat about every 10 minutes. When the paste is cool, it is beat one last time. The paste is poured into a bottle, seal and store at room temperature.

2. Process of Making a Natural Flower Sculpture

The plant is a rose flower and is treated in a low humidity environment. The cut end of the flower stem is immersed in an aqueous solution throughout the process. A red sable brush, number 12, is used to spread the paste over the surface of the flower petals. A first layer of the paste that is prepared by the process described in Example 1 is brushed on the petal surfaces using gentle and slow strokes to avoid damage to petals and other delicate plant tissues. The first layer is permitted to dry at room temperature for about 15 to 20 minutes. The transition of the paste from white to clear indicates sufficient dryness to begin applying subsequent layers. Three additional layers of paste are spread on top of the first layer in the same manner used to apply the first layer, permitting drying of layers between applications.

The stem is then removed from the water. The stem treated with paste in the same manner as the petals.

The final product is achieved by allowing the paste to harden for about one week into a firm encasement. The sculpture is set on wax paper during the drying period.

The natural plant sculpture or the present invention may be used as ornamental objects, either alone or to decorate other items, such as vases, lamps, containers, etc. In one embodiment, the sculptures is included in jewelry. The method presents a means to permanently keep plants.

The present invention has been described above in varied detail by reference to the particular embodiments. However, these specifics should not be construed as limitations on the scope of the invention, but merely as illustrations of some of the presently preferred embodiments. It is to be further understood that other modifications or substitutions may be made to the described information transfer system as well as methods of its use without departing from the broad scope of the invention. Therefore, the scope of the invention should be determined by the following claims and their legal equivalents.

What is claimed is:

1. A method for making a natural plant sculpture comprising:

spreading a paste over a surface of a plant, the paste including an adhesive, a synthetic latex resin prepared by emulsion polymerization, and a thickener, and drying the paste to form an inflexible and air-tight encasement.

2. The method of claim 1, wherein the latex is selected from the group comprising homopolymers and copolymers of vinyl esters, acrylate and methacrylate esters, maleic acid, maleic anhydride and maleic acid esters.

3. The method of claim 1, wherein the latex is a vinyl acetate resin emulsion.

4. The method of claim 2, wherein the thickener is starch and the adhesive is glue.

5. The method of claim 1, wherein steps a) and b) are repeated until a desired thickness of encasement to produce an inflexible and air-tight seal is achieved.

6. The method of claim 5, wherein steps a) and b) are repeated between 2 and 5 times.

7. The method of claim 1, wherein the encasement is between about 0.50 mm to 5.00 mm.

8. The method of claim 1, wherein the paste is viscous and the spreading is by using a utensil.

9. The method of claim 1, further comprising spreading paint over the dried encasement.

10. The method of claim 1, further comprising coating a water-insoluble sealer over the dried encasement.

11. The method of claim 1, wherein a portion of the plant that is untreated with paste is contacted with an aqueous solution during the spreading of paste.

12. The method of claim 1, wherein the paste is made by mixing the latex emulsion and adhesive with warm thickener to form a viscous consistency.

13. A method for making a natural plant sculpture comprising:

spreading a layer of paste over the plant surface, the paste including an adhesive, a synthetic resin prepared by emulsion polymerization, and a thickener;

drying the paste; and repeating steps a and b for a sufficient number of times to form an inflexible and air-tight encasement.

14. The method of claim 13, wherein the synthetic resin is selected from the group comprising homopolymers and copolymers of vinyl esters, acrylate and methacrylate esters, maleic acid, maleic anhydride and maleic acid esters.

15. The method of claim 13, wherein the synthetic resin is a vinyl acetate resin emulsion.

16. The method of claim 13, wherein the encasement is between about 0.50 mm to 5.00 mm.

17. The method of claim 13, wherein the paste is viscous and the spreading by using a utensil.

* * * * *